US011312980B2

(12) United States Patent
Nonaka et al.

(10) Patent No.: US 11,312,980 B2
(45) Date of Patent: Apr. 26, 2022

(54) METHOD FOR PRODUCING 3-HYDROXY-4-AMINOBENZOIC ACID COMPOUND

(71) Applicant: Kao Corporation, Tokyo (JP)

(72) Inventors: Kyoshiro Nonaka, Wakayama (JP); Fumikazu Takahashi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/269,689

(22) PCT Filed: Sep. 6, 2019

(86) PCT No.: PCT/JP2019/035142

§ 371 (c)(1),
(2) Date: Feb. 19, 2021

(87) PCT Pub. No.: WO2020/054598

PCT Pub. Date: Mar. 19, 2020

(65) Prior Publication Data

US 2021/0317484 A1 Oct. 14, 2021

(30) Foreign Application Priority Data

Sep. 13, 2018 (JP) ............................ JP2018-171849

(51) Int. Cl.
*C12P 13/00* (2006.01)
*C12N 9/02* (2006.01)
*C12N 1/21* (2006.01)

(52) U.S. Cl.
CPC .......... *C12P 13/001* (2013.01); *C12N 9/0073* (2013.01); *C12P 13/008* (2013.01); *C12Y 114/13002* (2013.01)

(58) Field of Classification Search
None
See application file for complete search history.

(56) References Cited

U.S. PATENT DOCUMENTS

2011/0137007 A1 6/2011 Suzuki et al.

FOREIGN PATENT DOCUMENTS

| | | | |
|---|---|---|---|
| JP | 2001-316340 | A | 11/2001 |
| JP | 3821350 | B | 9/2006 |
| JP | 5445453 | B2 | 1/2014 |

OTHER PUBLICATIONS

Genbank, Accession No. CP023313.2, Feb. 2018, www.ncbi.nlm.nih.gov. (Year: 2018).*

Uniprot, Accession No. Q9A5P3, 2018, www.uniprot.org. (Year: 2018).*

Uniprot, Accession No. P00438, 2018, ww.uniprot.org. (Year: 2018).*

Chen et al., Rational Engineering of p-Hydroxybenzoate Hydroxylase to Enable Efficient Gallic Acid Synthesis via a Novel Artificial Biosynthetic Pathway, Biotechnol. Bioeng. 114, 2017, 2571-80. (Year: 2017).*

Puigbo et al., Optimizer: a web server for optimizing the codon usage of DNA sequences, Nucleic Acids Res. 35, 2007, W126-W131. (Year: 2007).*

Represent. Merriam-Webster.com Dictionary, Merriam-Webster, www.merriam-webster.com/dictionary/represent. Accessed Oct. 22, 2021. (Year: 2021).*

International Search Report for PCT/JP2019/035142; I.A. fd Sep. 6, 2019, dated Nov. 19, 2019 from the Japan Patent Office, Tokyo, Japan.

International Preliminary Report on Patentability (IPRP), Chapter I of the Patent Cooperation Treaty, including the Written Opinion, for PCT/JP2019/035142; I.A. fd Sep. 6, 2019, dated Mar. 9, 2021, by the International Bureau of WIPO, Geneva, Switzerland.

Murase, H., "Structure and Properties of PBO Fiber," Sen'i Gakkaishi vol. 66, No. 6 (2010), pp. 176-180.

Mathias, LJ et al., "Two-step synthesis of alkyl- and alkenylbenzoxazole polymers," Macromolecules 18:616-622 (1985).

Entsch B et al., "para-Hydroxybenzoate hydroxylase containing 6-hydroxy-FAD is an effective enzyme with modified reaction mechanisms." J Biol Chem. May 5, 1987;262(13):6060-8. PMID: 3571246.

Gatti, DL et al., "pH-dependent structural changes in the active site of p-hydroxybenzoate hydroxylase point to the importance of proton and water movements during catalysis." Biochemistry. Jan. 16, 1996;35(2):567-78. doi: 10.1021/bi951344i. PMID: 8555229.

Ohta, Y et al., "Chain-growth condensation polymerization approach to synthesis of well-defined polybenzoxazole: Importance of higher reactivity of 3-amino-4-hydroxybenzoic acid ester compared to 4-amino-3-hydroxybenzoic acid ester," J. Polym. Sci. Part A: Polym. Chem., 52: 1730-1736 (2014). First published: Apr. 3, 2014, https://doi.org/10.1002/pola.27174.

(Continued)

*Primary Examiner* — Robert B Mondesi
*Assistant Examiner* — Todd M Epstein
(74) *Attorney, Agent, or Firm* — Sterne, Kessler, Goldstein & Fox P.L.L.C.

(57) ABSTRACT

Provided is a method for manufacturing a 3-hydroxy-4-aminobenzoic acid by using a microorganism. The method for manufacturing a 3-hydroxy-4-aminobenzoic acid comprises a step of bringing a 4-aminobenzoic acid into contact with a microorganism that produces the following polypeptide (A) or (B): (A) a polypeptide consisting of an amino acid sequence shown in SEQ ID NO: 2 or a polypeptide consisting of an amino acid sequence that has at least 90% identity to the amino acid sequence shown in SEQ ID NO: 2 and has 4-hydroxybenzoate hydroxylase activity, (B) a polypeptide consisting of an amino acid sequence shown in SEQ ID NO: 6 or a polypeptide consisting of an amino acid sequence that has at least 90% identity to the amino acid sequence shown in SEQ ID NO: 6 and has 4-hydroxybenzoate hydroxylase activity.

13 Claims, No Drawings

Specification includes a Sequence Listing.

(56) References Cited

OTHER PUBLICATIONS

P-hydroxybenzoate hydroxylase [Caulobacter vibrioides CB15], Database Genbank, Accession No. AAK24375.1 [online] retrieval date Oct. 30, 2019, internet:<URL:https://www.ncbi.nlm.nih.gov/protein/AAK24375.1>, Jan. 31, 2014.
4-hydoxybenzoate 3-monooxygenase [Novosphingobium aromaticvorans DSM 12444], Database Genbank, Accession No. ABD26872.1 [online] retrieval date Oct. 30, 2019, internet:<URL:https://www.ncbi.nlm.nih.gov/protein/ABD26872.1>, Jan. 28, 2014.

* cited by examiner

SEQUENCE LISTING

```
<160> NUMBER OF SEQ ID NOS: 16

<210> SEQ ID NO 1
<211> LENGTH: 1176
<212> TYPE: DNA
<213> ORGANISM: Artificial Sequence
<220> FEATURE:
<223> OTHER INFORMATION: Codon-optimized oligonucleotide

<400> SEQUENCE: 1

atgcgcactc aggtggctat cgtaggagca ggcccagctg gcctgttctt gggccatctc      60

ctccgtcaag ctggtgtgga cgtcgtgatt ctggaacgca aagaccgtgc ttatgtcgaa     120

ggccgagttc gggctggtgt cctggaacgt atcacggtgg agctgatgga gcgtcttggt     180

gtggatgagc gaatgcgccg agagggcttg gtgcatgctg gcgctaatct tgcgtctgat     240

ggcgagatgt tccgtatcga catggcagag ctcacgggtg gttccaccgt catggtttac     300

ggccaacagg aggtgatgaa ggacctgttt gatgcagcag agcagcgcga tctgcgaatt     360

gtctttgacg ccgatgcagt gcgtctgcac gatgtggaag gcgaacgtcc tcacatcacc     420

tggcgcaaag acggggcaga acaccgcctg gactgcgatt tcattgccgg ctgcgacggc     480
```

-continued

```
taccacggag tttctcgtgc gaccattccc gataaggttc tcaagacctt cgaacgggtg    540

tatccctttg ggtggttggg aatcctggct gaagcacctc cgtgtgacca cgagttgatc    600

tactcgaacc atgatcgcgg ttttgccctg gcgtcgatgc gctcaccgac acgctcccgc    660

tattacgtgc agtgctcact cgacgatcgc ctcgaggatt ggtccgatga acggttctgg    720

gatgaagttt cggttcgcct gggaccggaa gcagccgctc ggatcgttcg cgcaccttcc    780

ttcgagaaga gcattgcccc acttcgctcc ttcgtttccg agcctatgcg gtatggccgc    840

cttttcctcg cgggtgatgc ggctcatatc gttccaccca ctggagcgaa agggatgaac    900

ttggccgtat cagacgtcat catgctgtcc gaagccctgg tcgaacacta ccacgaacgc    960

tcttccgctg gtatcgatgg ttacagcgca cgtgcacttg cccgcgtctg gaaggcggag   1020

cgtttcagct ggtggtttac ctcccttact caccgcttcc cagaccagga cggcttcgac   1080

cgcaagatgc aagtcgccga attggcatac atcaagggtt ctcgcgctgc ccaggtcacc   1140

ctggcggaga actacgtagg actgccactc gtataa                             1176
```

```
<210> SEQ ID NO 2
<211> LENGTH: 391
<212> TYPE: PRT
<213> ORGANISM: Caulobacter vibrioides

<400> SEQUENCE: 2

Met Arg Thr Gln Val Ala Ile Val Gly Ala Gly Pro Ala Gly Leu Phe
1               5                   10                  15

Leu Gly His Leu Leu Arg Gln Ala Gly Val Asp Val Val Ile Leu Glu
            20                  25                  30

Arg Lys Asp Arg Ala Tyr Val Glu Gly Arg Val Arg Ala Gly Val Leu
        35                  40                  45

Glu Arg Ile Thr Val Glu Leu Met Glu Arg Leu Gly Val Asp Glu Arg
    50                  55                  60

Met Arg Arg Glu Gly Leu Val His Ala Gly Ala Asn Leu Ala Ser Asp
65                  70                  75                  80

Gly Glu Met Phe Arg Ile Asp Met Ala Glu Leu Thr Gly Gly Ser Thr
                85                  90                  95

Val Met Val Tyr Gly Gln Gln Glu Val Met Lys Asp Leu Phe Asp Ala
            100                 105                 110

Ala Glu Gln Arg Asp Leu Arg Ile Val Phe Asp Ala Asp Ala Val Arg
        115                 120                 125

Leu His Asp Val Glu Gly Glu Arg Pro His Ile Thr Trp Arg Lys Asp
    130                 135                 140

Gly Ala Glu His Arg Leu Asp Cys Asp Phe Ile Ala Gly Cys Asp Gly
145                 150                 155                 160

Tyr His Gly Val Ser Arg Ala Thr Ile Pro Asp Lys Val Leu Lys Thr
                165                 170                 175

Phe Glu Arg Val Tyr Pro Phe Gly Trp Leu Gly Ile Leu Ala Glu Ala
            180                 185                 190

Pro Pro Cys Asp His Glu Leu Ile Tyr Ser Asn His Asp Arg Gly Phe
        195                 200                 205

Ala Leu Ala Ser Met Arg Ser Pro Thr Arg Ser Arg Tyr Tyr Val Gln
    210                 215                 220

Cys Ser Leu Asp Asp Arg Leu Glu Asp Trp Ser Asp Glu Arg Phe Trp
225                 230                 235                 240

Asp Glu Val Ser Val Arg Leu Gly Pro Glu Ala Ala Ala Arg Ile Val
                245                 250                 255
```

```
Arg Ala Pro Ser Phe Glu Lys Ser Ile Ala Pro Leu Arg Ser Phe Val
            260                 265                 270

Ser Glu Pro Met Arg Tyr Gly Arg Leu Phe Leu Ala Gly Asp Ala Ala
        275                 280                 285

His Ile Val Pro Pro Thr Gly Ala Lys Gly Met Asn Leu Ala Val Ser
    290                 295                 300

Asp Val Ile Met Leu Ser Glu Ala Leu Val Glu His Tyr His Glu Arg
305                 310                 315                 320

Ser Ser Ala Gly Ile Asp Gly Tyr Ser Ala Arg Ala Leu Ala Arg Val
                325                 330                 335

Trp Lys Ala Glu Arg Phe Ser Trp Trp Phe Thr Ser Leu Thr His Arg
            340                 345                 350

Phe Pro Asp Gln Asp Gly Phe Asp Arg Lys Met Gln Val Ala Glu Leu
        355                 360                 365

Ala Tyr Ile Lys Gly Ser Arg Ala Ala Gln Val Thr Leu Ala Glu Asn
    370                 375                 380

Tyr Val Gly Leu Pro Leu Val
385                 390


<210> SEQ ID NO 3
<211> LENGTH: 1185
<212> TYPE: DNA
<213> ORGANISM: Artificial Sequence
<220> FEATURE:
<223> OTHER INFORMATION: Codon-optimized oligonucleotide

<400> SEQUENCE: 3

atgaaaactc aggtggctat cattggcgcg ggtccgtccg gactcctcct tgggcagttg      60

ctgcacaaag ctgggattga caacgtcatt ctcgagcgac agaccccaga ctatgttctg     120

ggacgcatcc gcgctggcgt cttggagcaa ggtatggttg acctgttgcg ggaagcagga     180

gtcgaccgtc gaatggcacg cgatggcctg gtacacgaag gagtcgaaat cgcattcgcg     240

ggtcaacgcc gccgtatcga cctgaagcgc ctgtctggcg gcaagaccgt aaccgtctat     300

ggtcagacgg aagtgacccg tgacctgatg gaggctcgag aagcatgtgg tgctaccacc     360

gtttaccagg ctgcggaggt tcgcctccac gatcttcaag gcgaacgccc gtatgtgacc     420

ttcgaacgcg atggtgagcg cttgcgcctt gattgcgact atatcgctgg atgcgatggc     480

ttccacggga tttcccggca atccatccct gcggaacgcc tgaaagtgtt cgagcgggtc     540

tacccgttcg ggtggctcgg tctgcttgct gacactccac cagtgtctca cgaactcatc     600

tacgccaacc atcctcgtgg tttcgcgttg tgctcacaac gttcagccac tcgctcgcgt     660

tactacgtac aggttccact ctccgaaaag gtggaggatt ggtccgacga gcgcttttgg     720

accgaactca aagcacgtct gccctctgag gtcgcggaga agttggttac tggcccctct     780

ttggagaaga gcattgcccc actgcgctcg tttgtcgtgg aacccatgca gcatggacgc     840

ctgtttctgg ccggcgatgc agcacacatc gtgcctccaa caggtgccaa gggccttaat     900

ctcgcggcat ccgatgtgtc gaccctctat cgtctgctgc ttaaggcata ccgggaaggc     960

cgtggcgagc ttcttgaacg gtactccgcc atctgtctgc gccgtatctg gaaggccgaa    1020

cgcttctcct ggtggatgac gagcgttctg catcgctttc cggataccga tgccttctcc    1080

cagcgaattc agcagacgga actcgagtac tacttgggca gcgaagctgg tctggctaca    1140

atcgcagaga actacgttgg cctgccttac gaggagatcg agtaa                    1185
```

-continued

<210> SEQ ID NO 4
<211> LENGTH: 394
<212> TYPE: PRT
<213> ORGANISM: Pseudomonas aeruginosa

<400> SEQUENCE: 4

```
Met Lys Thr Gln Val Ala Ile Ile Gly Ala Gly Pro Ser Gly Leu Leu
1               5                   10                  15

Leu Gly Gln Leu Leu His Lys Ala Gly Ile Asp Asn Val Ile Leu Glu
            20                  25                  30

Arg Gln Thr Pro Asp Tyr Val Leu Gly Arg Ile Arg Ala Gly Val Leu
        35                  40                  45

Glu Gln Gly Met Val Asp Leu Leu Arg Glu Ala Gly Val Asp Arg Arg
    50                  55                  60

Met Ala Arg Asp Gly Leu Val His Glu Gly Val Glu Ile Ala Phe Ala
65                  70                  75                  80

Gly Gln Arg Arg Arg Ile Asp Leu Lys Arg Leu Ser Gly Gly Lys Thr
                85                  90                  95

Val Thr Val Tyr Gly Gln Thr Glu Val Thr Arg Asp Leu Met Glu Ala
            100                 105                 110

Arg Glu Ala Cys Gly Ala Thr Thr Val Tyr Gln Ala Ala Glu Val Arg
        115                 120                 125

Leu His Asp Leu Gln Gly Glu Arg Pro Tyr Val Thr Phe Glu Arg Asp
    130                 135                 140

Gly Glu Arg Leu Arg Leu Asp Cys Asp Tyr Ile Ala Gly Cys Asp Gly
145                 150                 155                 160

Phe His Gly Ile Ser Arg Gln Ser Ile Pro Ala Glu Arg Leu Lys Val
                165                 170                 175

Phe Glu Arg Val Tyr Pro Phe Gly Trp Leu Gly Leu Leu Ala Asp Thr
            180                 185                 190

Pro Pro Val Ser His Glu Leu Ile Tyr Ala Asn His Pro Arg Gly Phe
        195                 200                 205

Ala Leu Cys Ser Gln Arg Ser Ala Thr Arg Ser Arg Tyr Tyr Val Gln
    210                 215                 220

Val Pro Leu Ser Glu Lys Val Glu Asp Trp Ser Asp Glu Arg Phe Trp
225                 230                 235                 240

Thr Glu Leu Lys Ala Arg Leu Pro Ser Glu Val Ala Glu Lys Leu Val
                245                 250                 255

Thr Gly Pro Ser Leu Glu Lys Ser Ile Ala Pro Leu Arg Ser Phe Val
            260                 265                 270

Val Glu Pro Met Gln His Gly Arg Leu Phe Leu Ala Gly Asp Ala Ala
        275                 280                 285

His Ile Val Pro Pro Thr Gly Ala Lys Gly Leu Asn Leu Ala Ala Ser
    290                 295                 300

Asp Val Ser Thr Leu Tyr Arg Leu Leu Leu Lys Ala Tyr Arg Glu Gly
305                 310                 315                 320

Arg Gly Glu Leu Leu Glu Arg Tyr Ser Ala Ile Cys Leu Arg Arg Ile
                325                 330                 335

Trp Lys Ala Glu Arg Phe Ser Trp Trp Met Thr Ser Val Leu His Arg
            340                 345                 350

Phe Pro Asp Thr Asp Ala Phe Ser Gln Arg Ile Gln Gln Thr Glu Leu
        355                 360                 365

Glu Tyr Tyr Leu Gly Ser Glu Ala Gly Leu Ala Thr Ile Ala Glu Asn
    370                 375                 380
```

-continued

```
Tyr Val Gly Leu Pro Tyr Glu Glu Ile Glu
385                 390

<210> SEQ ID NO 5
<211> LENGTH: 1170
<212> TYPE: DNA
<213> ORGANISM: Artificial Sequence
<220> FEATURE:
<223> OTHER INFORMATION: Codon-optimized oligonucleotide

<400> SEQUENCE: 5

atgaaaaccc aggttgccat cattggtgca ggaccagcag gcttgttgct cggtcacttg     60

ctcaaagccg aaggaatcga ctgcgtggtg ctggagcgcc aaacgccaga ctacgtactt    120

ggacggattc gcgcgggtgt tctggagcag atcaccgtgg gtctgatgga acgtcttggc    180

ctggatgctc gactgaaggc tgagggcctg gttgaggagg gctttaacct tgccgatggc    240

gaacgcctca ttcgcatcga cgtcgctaac ttgactggca agactgtcgt ggtgtatggc    300

cagaccgaga tcaccaaaga cttgatggac gctgcacctg aacgtggcct ccaggttatc    360

tacggtgcta gcgaagtggc actgttcgac atcgagtccg atgcccctta tgtcacctac    420

gtccatgacg gggctcctcg tcgaattgat gcacggttca tcgttgggtg tgacggcttt    480

cacggtccgt cacgtaaggc gattccggct tcggtggccc gcgaatacga acgcgtctat    540

ccgtttgggt ggctcggcat cctcgcagat gttccaccat gcaatcacga gctgatctac    600

gccaatcacg aacgcggttt cgcgctggct tccatgcgtt cccacacgcg tagccgctat    660

tacgtagatg ttcccctcac tgagaaggtg gaagattggt ctgacgaacg catttgggac    720

gaactggcag tacgccttgg ccccgaagca gccgctaaca tcacacgagg tccttcgatc    780

gagaagtcca tcgctccgct tcggtcctac gtgttcgagc caatgcgcca tggttccctg    840

cttctgtgcg gagatgcagc gcacattgtc ccaccaacag gcgctaaagg cctgaacttg    900

gcggcctctg atgtgcacta tgcggcagaa gcactgaccg gattcttcaa gcgcgcagat    960

aacgatgcag ttccgcgtta cagcgccaaa gcgcttgctc gggtttggaa gtctgaacgc   1020

ttctcctggt cactgaccaa gctcatgcat cgcttccctg aggacggacc ctttgaacgt   1080

gccatgcaag tcgcagagct cgagtacatc gcgacctcca aggctgcgca gacctctatc   1140

gccgagaact acgtcggtct gcccgtctaa                                   1170

<210> SEQ ID NO 6
<211> LENGTH: 389
<212> TYPE: PRT
<213> ORGANISM: Novosphingobium aromaticivorans

<400> SEQUENCE: 6

Met Lys Thr Gln Val Ala Ile Ile Gly Ala Gly Pro Ala Gly Leu Leu
1               5                   10                  15

Leu Gly His Leu Leu Lys Ala Glu Gly Ile Asp Cys Val Val Leu Glu
            20                  25                  30

Arg Gln Thr Pro Asp Tyr Val Leu Gly Arg Ile Arg Ala Gly Val Leu
        35                  40                  45

Glu Gln Ile Thr Val Gly Leu Met Glu Arg Leu Gly Leu Asp Ala Arg
    50                  55                  60

Leu Lys Ala Glu Gly Leu Val Glu Glu Gly Phe Asn Leu Ala Asp Gly
65                  70                  75                  80

Glu Arg Leu Ile Arg Ile Asp Val Ala Asn Leu Thr Gly Lys Thr Val
                85                  90                  95
```

-continued

```
Val Val Tyr Gly Gln Thr Glu Ile Thr Lys Asp Leu Met Asp Ala Ala
            100                 105                 110

Pro Glu Arg Gly Leu Gln Val Ile Tyr Gly Ala Ser Glu Val Ala Leu
        115                 120                 125

Phe Asp Ile Glu Ser Asp Ala Pro Tyr Val Thr Tyr Val His Asp Gly
    130                 135                 140

Ala Pro Arg Arg Ile Asp Ala Arg Phe Ile Val Gly Cys Asp Gly Phe
145                 150                 155                 160

His Gly Pro Ser Arg Lys Ala Ile Pro Ala Ser Val Ala Arg Glu Tyr
                165                 170                 175

Glu Arg Val Tyr Pro Phe Gly Trp Leu Gly Ile Leu Ala Asp Val Pro
            180                 185                 190

Pro Cys Asn His Glu Leu Ile Tyr Ala Asn His Glu Arg Gly Phe Ala
        195                 200                 205

Leu Ala Ser Met Arg Ser His Thr Arg Ser Arg Tyr Tyr Val Asp Val
    210                 215                 220

Pro Leu Thr Glu Lys Val Glu Asp Trp Ser Asp Glu Arg Ile Trp Asp
225                 230                 235                 240

Glu Leu Ala Val Arg Leu Gly Pro Glu Ala Ala Ala Asn Ile Thr Arg
                245                 250                 255

Gly Pro Ser Ile Glu Lys Ser Ile Ala Pro Leu Arg Ser Tyr Val Phe
            260                 265                 270

Glu Pro Met Arg His Gly Ser Leu Leu Leu Cys Gly Asp Ala Ala His
        275                 280                 285

Ile Val Pro Pro Thr Gly Ala Lys Gly Leu Asn Leu Ala Ala Ser Asp
    290                 295                 300

Val His Tyr Ala Ala Glu Ala Leu Thr Gly Phe Phe Lys Arg Ala Asp
305                 310                 315                 320

Asn Asp Ala Val Pro Arg Tyr Ser Ala Lys Ala Leu Ala Arg Val Trp
                325                 330                 335

Lys Ser Glu Arg Phe Ser Trp Ser Leu Thr Lys Leu Met His Arg Phe
            340                 345                 350

Pro Glu Asp Gly Pro Phe Glu Arg Ala Met Gln Val Ala Glu Leu Glu
        355                 360                 365

Tyr Ile Ala Thr Ser Lys Ala Ala Gln Thr Ser Ile Ala Glu Asn Tyr
    370                 375                 380

Val Gly Leu Pro Val
385
```

<210> SEQ ID NO 7
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 7
gaaggagata tacatatgcg cactcaggtg gctat 35

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 8

-continued gtggtggtgg tggtgttata cgagtggcag tccta 35

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 9
gaaggagata tacatatgaa aactcaggtg gctat 35

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 10
gtggtggtgg tggtgttact cgatctcctc gtaag 35

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 11
gaaggagata tacatatgaa aacccaggtt gccat 35

<210> SEQ ID NO 12
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 12
gtggtggtgg tggtgttaga cgggcagacc gacgt 35

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 13
atgtatatct ccttcttaaa gttaaac 27

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
caccaccacc accaccactg agatc 25

<210> SEQ ID NO 15
<211> LENGTH: 34
<212> TYPE: DNA
<213> ORGANISM: Artificial Sequence -continued

```
<220> FEATURE:
<223> OTHER INFORMATION: Synthetic oligonucleotide

<400> SEQUENCE: 15

cgaaattaat acgactcact ataggggaat tgtg                    34


<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 16

ccaaggggtt atgctagtta ttgctcag                           28
```

METHOD FOR PRODUCING 3-HYDROXY-4-AMINOBENZOIC ACID COMPOUND

FIELD OF THE INVENTION

The present invention relates to a method for producing 3-hydroxy-4-aminobenzoic acids by using a microorganism.

BACKGROUND OF THE INVENTION

Polybenzoxazole (PBO) is known as an engineering plastic having excellent heat resistance and mechanical strength and is used as, for example, fiber materials or insulating films of semiconductor devices (Non Patent Literature 1).

A benzoxazole structure is generated by condensation of an o-aminophenol functional group and a carboxylic acid. Accordingly, it is expected that 3-hydroxy-4-aminobenzoic acids (HABAs) having these functional groups in the molecules are useful as monomers for PBO. Actually, synthesis of polybenzoxazoles using HABAs and physical property evaluation have been investigated (Non Patent Literature 2).

In recent years, attention has been paid to methods for manufacturing compounds by microbial fermentation using recyclable resources as raw materials for, for example, reduction of global environmental impact. For example, production of 3-amino-4-hydroxybenzoic acid (AHBA) having a structure similar to HABA by a microorganism and polymerization thereof have been investigated (Patent Literature 1).

Regarding manufacturing of HABA, for example, a synthetic method through chemical reduction of a nitro aromatic compound has been known so far (Patent Literature 2). As a method to enable HABA fermentation production by a microbial method, hydroxylation of the 3-position of 4-aminobenzoic acid (ABA), which can be biosynthesized in microorganisms, is conceived, but it has been only reported that some 4-hydroxybenzoate hydroxylases have a slight activity regarding such a reaction (Non Patent Literatures 3 and 4).

PATENT LITERATURE

[Patent Literature 1] JP-B-5445453
[Patent Literature 2] JP-B-3821350

NON PATENT LITERATURE

[Non Patent Literature 1] Hiroki MURASE, Sen'i Gakkaishi, Vol. 66, No. 6 (2010)
[Non Patent Literature 2] Lon J. Mathias, et al., Macromolecules, Vol. 18, No. 4, pp. 616-622 (1985)
[Non Patent Literature 3] Barrie Entsch, et al., The Journal of Biological Chemistry, Vol. 262, No. 13, pp. 6060-6068 (1987)
[Non Patent Literature 4] Domenico L. Gatti, et Biochemistry, Vol. 35, No. 2, pp. 567-578 (1996)

SUMMARY OF THE INVENTION

The present invention relates to the following:

A method for manufacturing a 3-hydroxy-4-aminobenzoic acid, comprising a step of bringing a 4-aminobenzoic acid into contact with a microorganism that produces the following polypeptide (A) or (B):

(A) a polypeptide consisting of the amino acid sequence shown in SEQ ID NO: 2 or a polypeptide consisting of an amino acid sequence that has at least 90% identity to the amino acid sequence shown in SEQ ID NO: 2 and has 4-hydroxybenzoate hydroxylase activity;

(B) a polypeptide consisting of the amino acid sequence shown in SEQ ID NO: 6 or a polypeptide consisting of an amino acid sequence that has at least 90% identity to the amino acid sequence shown in SEQ ID NO: 6 and has 4-hydroxybenzoate hydroxylase activity.

DETAILED DESCRIPTION OF THE INVENTION

The present invention relates to provide a method for manufacturing a 3-hydroxy-4-aminobenzoic acid by using a microorganism.

The present inventors have found that the 3-position of 4-aminobenzoic acid (ABA) can be efficiently hydroxylated by using a microorganism that produces a specific 4-hydroxybenzoate hydroxylase.

According to the present invention, a 3-hydroxy-4-aminobenzoic acid can be efficiently manufactured.

(1) Definition

In the present specification, the identity of an amino acid sequence or a nucleotide sequence is calculated by Lipman-Pearson method (Science, 1985, 227: 1435-1441). Specifically, the identity is calculated by using the homology analysis (Search homology) program of genetic information processing software GENETYX Ver. 12 and setting the unit size to compare (ktup) at 2.

In the present specification, "at least 90% identity" regarding an amino acid sequence or a nucleotide sequence refers to an identity of 90% or more, preferably 95% or more, more preferably 96% or more, even more preferably 97% or more, even more preferably 98% or more, and even more preferably 99% or more.

In the present specification, "amino acid sequence having deletion, substitution, addition, or insertion of one or more amino acids" refers to an amino acid sequence having deletion, substitution, addition, or insertion of 1 or more and 10 or less, preferably 1 or more and 8 or less, more preferably 1 or more and 5 or less, and even more preferably 1 or more and 3 or less amino acids. In addition, in the present specification, "nucleotide sequence having deletion, substitution, addition, or insertion of one or more nucleotides" refers to a nucleotide sequence having deletion, substitution, addition, or insertion of 1 or more and 30 or less, preferably 1 or more and 24 or less, more preferably 1 or more and 15 or less, and even more preferably 1 or more and 9 or less nucleotides. In the present specification, the "addition" of amino acid(s) or nucleotide(s) includes addition of amino acid(s) or nucleotide(s) to one end and both ends of the sequence.

In the present specification, "operable linkage" between a regulatory region and a gene refers to that a gene and a regulatory region are linked to each other such that the gene can be expressed under control of the regulatory region. The procedure of "operable linkage" between a gene and a regulatory region is well known to those skilled in the art.

In the present specification, the term "original" used for function, property, and trait of a cell is used for expressing that the function, property, and trait are present in the wild-type of the cell. In contrast, the term "exogenous" is used for expressing function, property, and trait that are not originally present in the cell but are introduced from the outside. For example, an "exogenous" gene or polynucleotide is a gene or polynucleotide introduced into a cell from the outside. The exogenous gene or polynucleotide may be derived from homogenous biological species of the cell into which the gene or polynucleotide is introduced or derived from different biological species (i.e., heterologous gene or polynucleotide).

(2) Manufacture of 3-hydroxy-4-aminobenzoic acid

The method of the present invention is a method for manufacturing a 3-hydroxy-4-aminobenzoic acid from a 4-aminobenzoic acid by using a microorganism.

Specific examples of the 4-aminobenzoic acid include a 4-aminobenzoic acid derivative represented by the following Formula (1):

(1)

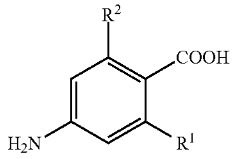

wherein $R^1$ represents a hydrogen atom, a hydroxy group (—OH), a methoxy group (—$OCH_3$), an amino group (—$NH_2$), a fluorine atom (—F), a chlorine atom (—Cl), a bromine atom (—Br), a iodine atom (—I), a carboxy group (—COOH), a methyl group (—$CH_3$), or an ethyl group (—$CH_2CH$); and $R^2$ represents a hydrogen atom, a hydroxy group (—OH), a methoxy group (—$OCH_3$), an amino group (—$NH_2$), a fluorine atom (—F), a chlorine atom (—Cl), a bromine atom (—Br), a iodine atom (—I), a carboxy group (—COOH), a methyl group (—$CH_3$), or an ethyl group (—$CH_2CH_3$),
and specific examples of the 3-hydroxy-4-aminobenzoic acid include a 3-hydroxy-4-aminobenzoic acid derivative represented by the following Formula (2):

(2)

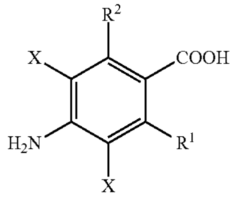

wherein $R^1$ and $R^2$ represent the same as above; and one of Xs represents a hydrogen atom, and the other represents a hydroxy group.

The functional group represented by $R^1$ is preferably a hydrogen atom, a hydroxy group (—OH), a methoxy group (—$OCH_3$), a fluorine atom (—F), or a methyl group (—$CH_3$).

The functional group represented by $R^2$ is preferably a hydrogen atom, a hydroxy group (—OH), a methoxy group (—$OCH_3$), a fluorine atom (—F), or a methyl group (—$CH_3$).

More preferably, $R^1$ and $R^2$ are both hydrogen atoms.

The microorganism used in the present invention is a microorganism that produces the following polypeptide (A) or (B) (hereinafter, also referred to as "polypeptide of the present invention"):

(A) a polypeptide consisting of the amino acid sequence shown in SEQ ID NO: 2 or a polypeptide consisting of an amino acid sequence that has at least 90% identity to the amino acid sequence shown in SEQ ID NO: 2 and has 4-hydroxybenzoate hydroxylase activity;

(B) a polypeptide consisting of the amino acid sequence shown in SEQ ID NO: 6 or a polypeptide consisting of an amino acid sequence that has at least 90% identity to the amino acid sequence shown in SEQ ID NO: 6 and has 4-hydroxybenzoate hydroxylase activity.

Here, the polypeptide consisting of the amino acid sequence shown in SEQ ID NO:2 (also referred to as "HFM122") and the polypeptide consisting of the amino acid sequence shown in SEQ ID NO: 6 (also referred to as "HFM689") are known as 4-hydroxybenzoate-3-monooxygenases (EC 1.14.13.2).

Examples of the amino acid sequence that has at least 90% identity to the amino acid sequence shown in SEQ ID NO: 2 or 6 include amino acid sequences having deletion, substitution, addition, or insertion of one or more amino acids with respect to the amino acid sequence shown in SEQ ID NO: 2 or 6.

The "4-hydroxybenzoate hydroxylase activity" means catalytic activity shown by a 4-hydroxybenzoate hydroxylase, and the 4-hydroxybenzoate hydroxylase means an enzyme that catalyzes hydroxylation of 4-hydroxybenzoic acid, preferably a 4-hydroxybenzoate-3-monooxygenase that has catalytic activity of promoting either or both of the reaction of hydroxylating the 3-position of 4-hydroxybenzoic acid to generate protocatechuic acid and the reverse reaction thereof.

The 4-hydroxybenzoate hydroxylase activity can be determined by, for example, a known method (Yan Huang, et al., Appl. Microbiol. Bictechnol., 78, 75-83 (2008)).

Examples of the method for introducing a mutation such as deletion, substitution, addition, or insertion of amino acid(s) into an amino acid sequence include, for example, a method for introducing a mutation such as deletion, substitution, addition, or insertion of nucleotide(s) into a nucleotide sequence encoding the amino acid sequence. Examples of the method for introducing a mutation into a nucleotide sequence include mutagenesis with a chemical mutagen such as ethyl methanesulfonate, N-methyl-N-nitrosoguanidine, or nitrous acid, or a physical mutagen such as ultraviolet rays, X-rays, gamma-rays, or ion beams, site-directed mutagenesis, and the method described in Dieffenbach, et al. (Cold Spring Harbar Laboratory Press, New York, 581-621, 1995). Examples of the site-directed mutagenesis include a method utilizing splicing overlap extension (SOD) PCR (Horton, et al., Gene, 77, 61-68, 1989), an ODA method (Hashimoto-Gotoh, et al., Gene, 152, 271-276, 1995), and a Kunkel method (Kunkel, T. A., Proc. Natl. Acad. Sci. USA, 1985, 82, 488). Alternatively, a commercially available site-directed mutagenesis kit such as Site-Directed Mutagenesis System Mutan-SuperExpress Km Kit (Takara Bio Inc.), Transformer™ Site-Directed Mutagenesis Kit (Clontech), or KOD-Plus-Mutagenesis Kit (Toyobo Co., Ltd.), can also be used.

In the "microorganism that produces the polypeptide" of the present invention, the polypeptide is not limited to exogenous polypeptides, and those originally present in the microorganism are also included. The microorganism may be any microorganism that includes a polynucleotide required for expression of the polypeptide in an expressible state and is preferably a microorganism into which the polynucleotide is introduced expressibly or a microorganism in which the expression of the polynucleotide is enhanced, i.e., a genetically modified microorganism.

Here, examples of the polynucleotide include the following polynucleotide (a) or (b) (hereinafter, also referred to as "polynucleotide of the present invention"):

(a) a polynucleotide consisting of the nucleotide sequence shown in SEQ ID NO: 1 or a polynucleotide consisting of a nucleotide sequence that has at least 90% identity to the nucleotide sequence shown in SEQ ID NO: 1 and encodes a polypeptide having 4-hydroxybenzoate hydroxylase activity;

(b) a polynucleotide consisting of the nucleotide sequence shown in SEQ ID NO: 5 or a polynucleotide consisting of a nucleotide sequence that has at least 90% identity to the nucleotide sequence shown in SEQ ID NO: 5 and encodes a polypeptide having 4-hydroxybenzoate hydroxylase activity.

Examples of the nucleotide sequence having at least 90% identity to the nucleotide sequence shown in SEQ ID NO: 1 or 5 include nucleotide sequences obtained by deletion, substitution, addition, or insertion of one or more nucleotides with respect to the nucleotide sequence shown in SEQ ID NO: 1 or 5. The method for introducing a mutation such as deletion, substitution, addition, or insertion of nucleotide(s) into a nucleotide sequence is as described above. The polynucleotide can be in a single-strand form or a double-strand form and may be a DNA or an RNA. The DNA can be an artificial DNA, such as a cDNA and a chemically synthesized DNA.

The polynucleotide may be incorporated in a vector. Preferably, the vector containing the polynucleotide of the present invention is an expression vector. In addition, preferably, the vector is an expression vector that can introduce the polynucleotide of the present invention into a host microorganism and can express the polynucleotide in the host microorganism. Preferably, the vector includes the polynucleotide of the present invention and a regulatory region operably linked thereto. The vector may be a vector that can extrachromosomally and autonomously proliferate and replicate, for example, a plasmid or may be a vector incorporated intrachromosomally.

Specifically, examples of the vector include pBluescript II SK(−) (Stratagene), pUC vector (Takara Bio Inc.) such as pUC18/19 or pUC118/119, pET vector (Takara Bio Inc.), pGEX vector (GE Healthcare), pCold vector (Takara Bio Inc.), pHY300PLK (Takara Bio Inc.), pUB110 (Mckenzie, T. et al., 1986, Plasmid, 15(2): 93-103), pBR322 (Takara Bio Inc.), pRS403 (Stratagene), pMW218/219 (Nippon Gene Co., Ltd.), pRI vector (Takara Bio Inc.) such as pRI909/910, pBI vector (Clontech), IN3 vector (Inplanta innovations Inc.), pPTR1/2 (Takara Bio Inc.), pDJB2 (D. J. Balance, et al., Gene, 36, 321-331, 1985), pAB4-1 (van Hartingsveldt W., et al., Mol. Gen. Genet., 206, 71-75, 1987), pLeu4 (M. I. G. Roncero, et al., Gene, 84, 335-343, 1989), pPyr225 (C. D. Skory, et al., Mol. Genet. Genomics, 268, 397-406, 2002), and pFG1 (Gruber, F., et al., Curr. Genet., 18, 447-451, 1990).

In addition, the polynucleotide may be constructed as a DNA fragment containing the polynucleotide. Examples of the DNA fragment include a PCR-amplified DNA fragment and a restriction enzyme-cleaved DNA fragment. Preferably, the DNA fragment can be an expression cassette including the polynucleotide of the present invention and a regulatory region operably linked thereto.

The regulatory region contained in the vector or the DNA fragment is a sequence for expressing the polynucleotide of the present invention in a host cell into which the vector or the DNA fragment has been introduced, and examples thereof include an expression-regulatory region such as promoter and terminator, and a replication origin. The type of the regulatory region can be appropriately selected according to the type of the host microorganism into which the vector or a DNA fragment is introduced. The vector or the DNA fragment may further include a selection marker such as an antibiotic-resistance gene or an amino acid synthesis-related gene, as needed.

The means for introducing the polynucleotide of the present invention expressibly into a host cell or enhancing the expression of the polynucleotide of the present invention therein includes, for example, introduction of the vector or the DNA fragment containing the polynucleotide of the present invention operably linked to a regulatory region, preferably a strong regulatory region (regulatory region that can enhance the expression compared to the wild-type), into a host microorganism, or arrangement of a strong regulatory region and the polynucleotide of the present invention operably linked to each other on the genome of a host microorganism (e.g., replacement of the regulatory region sequence of the polynucleotide of the present invention on the genome of the parent cell with the strong regulatory region).

Although any of fungi, yeast, actinomycete, *Escherichia coli, Bacillus subtilis*, and the like may be used as the host cell, *Escherichia coli* and actinomycete are preferable. Examples of the actinomycete include *Corynebacterium, Mycobacterium, Rhodococcus, Streptomyces*, and *Propionibacterium*, preferably *Corynebacterium* and more preferably *Corynebacterium glutamicum.*

In the introduction of the vector or the DNA fragment into the microorganism, a general transformation method, for example, an electroporation method, a transformation method, a transfection method, a conjugation method, a protoplast method, a particle gun method, and an *agrobacterium* method, can be used.

The microorganism into which a target vector or DNA fragment has been introduced can be selected utilizing a selection marker. For example, when the selection marker is an antibiotic-resistance gene, a microorganism (transformant) into which the target vector or DNA fragment has been introduced can be selected by culturing the microorganism in a culture medium containing the antibiotic. In addition, for example, when the selection marker is an amino acid synthesis-related gene, the gene is transferred into an amino acid-auxotrophic host microorganism and thereafter, a microorganism into which the target vector or DNA fragment has been introduced can be selected using, as an indicator, presence or absence of the amino acid auxotrophy. Alternatively, it is also possible to verify the introduction of the target vector or DNA fragment by investigating the DNA sequence of a transformant by, for example, PCR.

In addition, examples of the strong regulatory region include known high expression promoters such as 17 promoter, lac promoter, tac promoter, and trp promoter, but are not particularly limited thereto.

Examples of the method for replacing the regulatory region of the polynucleotide present on the genome of a host microorganism with a strong regulatory region include a method for introducing a DNA fragment including a strong regulatory region and a polynucleotide sequence of a selection marker into a host cell and selecting a microorganism transformed by homologous recombination or non-homologous recombination.

A useful strain that produces a 3-hydroxy-4-aminobenzoic acid can be obtained by culturing the thus-prepared microorganism that produces a polypeptide of the present invention, evaluating the productivity of the 3-hydroxy-4-aminobenzoic acid, and selecting an appropriate recombinant. The product can be measured according to the method described in the reference example below.

The method for manufacturing a 3-hydroxy-4-aminobenzoic acid of the present invention is carried out by bringing a 4-aminobenzoic acid into contact with the above-described microorganism that produces the polypeptide. The conditions for contact between the microorganism and the 4-aminobenzoic acid can be appropriately designed according to the microorganism to be used.

More specifically, the culture medium for culturing the microorganism of the present invention may be any of a natural medium or a synthetic medium as long as it contains a carbon source, a nitrogen source, inorganic salts, etc. and can efficiently culture the microorganism. Examples of the carbon source can include sugars such as glucose, polyols such as glycerol, alcohols such as ethanol, or organic acids such as pyruvic acid, succinic acid, and citric acid. In addition, examples of the nitrogen source can include peptone, meat extract, yeast extract, casein hydrolysate, soybean meal alkaline extract, alkyl amines such as methylamine, or ammonia or a salt thereof. Furthermore, for example, salts such as phosphate, carbonate, sulfate, magnesium, calcium, potassium, iron, manganese, and zinc, a specific amino acid, a specific vitamin, or an antifoam can be used as needed.

The culture can be usually performed at from 10° C. to 40° C., for from 6 to 72 hours, preferably from 9 to 60 hours, and more preferably from 12 to 48 hours, while stirring or shaking as needed. In addition, an antibiotic, such as ampicillin or kanamycin, may be added to the culture medium during culturing as needed.

The method for contact between the culture (including culture solution, culture supernatant, culture cells, and cell homogenate) and the 4-aminobenzoic acid is not particularly limited, and the contact may be performed during the culturing of the microorganism or may be separately performed after the culturing. In addition, the 4-aminobenzoic acid may be biosynthesized in cells during the culturing or may be added from the outside. Although the conditions for contact are not particularly limited, the contact can be usually performed at from 20° C. to 50° C., for from 5 minutes to 72 hours, preferably from 1 to 60 hours, and more preferably from 1 to 24 hours, while stirring or shaking as needed.

After the contact between the culture and the 4-aminobenzoic acid, when a 3-hydroxy-4-aminobenzoic acid is produced inside the cell, the 3-hydroxy-4-aminobenzoic acid can be extracted by a generally known method, for example, by destroying the cell through a mechanical method, an enzymatic method using lysozyme or the like, or a chemical treatment using a surfactant. In addition, when the 3-hydroxy-4-aminobenzoic acid is produced outside the cell, the culture solution is directly used, or the cell is removed by centrifugation or the like.

The method for collecting and isolating the 3-hydroxy-4-aminobenzoic acid from the culture is not particularly limited. More specifically, the collection and isolation can be carried out by combining well-known methods such as an ion exchange resin method, a precipitation method, a crystallization method, a recrystallization method, and a concentration method. For example, the 3-hydroxy-4-aminobenzoic acid can be obtained by removing cells by centrifugation or the like, then removing ionic materials with cation and anion exchange resins, and performing concentration. The 3-hydroxy-4-aminobenzoic acid accumulated in the culture may be directly used without isolation.

Regarding the above-described embodiments, the present invention further discloses the following aspects:

<1> A method for manufacturing a 3-hydroxy-4-aminobenzoic acid, comprising a step of bringing a 4-aminobenzoic acid into contact with a microorganism that produces the following polypeptide (A) or (B):

(A) a polypeptide consisting of an amino acid sequence shown in SEQ ID NO: 2 or a polypeptide consisting of an amino acid sequence that has at least 90% identity to the amino acid sequence shown in SEQ ID NO: 2 and has 4-hydroxybenzoate hydroxylase activity;

(B) a polypeptide consisting of an amino acid sequence shown in SEQ ID NO: 6 or a polypeptide consisting of an amino acid sequence that has at least 90% identity to the amino acid sequence shown in SEQ ID NO: 6 and has 4-hydroxybenzoate hydroxylase activity.

<2> A method according to aspect <1>, wherein the microorganism comprises the following polynucleotide (a) or (b) in an expressible state:

(a) a polynucleotide consisting of a nucleotide sequence shown in SEQ ID NO: 1 or a polynucleotide consisting of a nucleotide sequence that has at least 90% identity to the nucleotide sequence shown in SEQ ID NO: 1 and encodes a polypeptide having 4-hydroxybenzoate hydroxylase activity;

(b) a polynucleotide consisting of a nucleotide sequence shown in SEQ ID NO: 5 or a polynucleotide consisting of a nucleotide sequence that has at least 90% identity to the nucleotide sequence shown in SEQ ID NO: 5 and encodes a polypeptide having 4-hydroxybenzoate hydroxylase activity.

<3> The method according to aspect <1> or <2>, wherein the microorganism is *Escherichia coli* or *Corynebacterium*.

<4> The method according to any of aspects <1> to <3>, wherein the 4-aminobenzoic acid is a 4-aminobenzoic acid derivative represented by the following Formula (1)

(1)

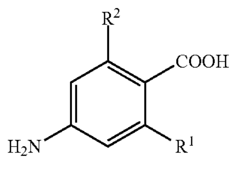

wherein $R^1$ represents a hydrogen atom, a hydroxy group (—OH), a methoxy group (—$OCH_3$), an amino group (—$NH_2$), a fluorine atom (—F), a chlorine atom (—Cl), a bromine atom (—Br), a iodine atom (—I), a carboxy group (—COOH), a methyl group (—CHS), or an ethyl group (—$CH_2CH$); and $R^2$ represents a hydrogen atom, a hydroxy group (—OH), a methoxy group (—$OCH_3$), an amino group (—$NH_2$), a fluorine atom (—F), a chlorine atom (—Cl), a bromine atom (—Br), a iodine atom (—I), a carboxy group (—COOH), a methyl group (—$CH_3$), or an ethyl group (—$CH_2CH_3$), and the 3-hydroxy-4-aminobenzoic acid is a 3-hydroxy-4-aminobenzoic acid derivative represented by the following Formula (2):

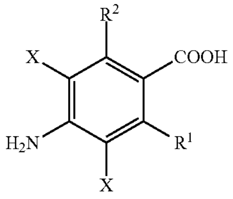

(2)

wherein $R^1$ and $R^2$ represent the same as above; and one of Xs represents a hydrogen atom, and the other represents a hydroxy group.

<5> The method according to aspect <4>, wherein in the 4-aminobenzoic acid derivative represented by Formula (1) and the 3-hydroxy-4-aminobenzoic acid derivative represented by Formula (2), $R^1$ is preferably a hydrogen atom, a hydroxy group (—OH), a methoxy group (—$OCH_3$), a fluorine atom (—F), or a methyl group (—$CH_3$), <6> The method according to aspect <4> or <5>, wherein in the 4-aminobenzoic acid derivative represented by Formula (1) and the 3-hydroxy-4-aminobenzoic acid derivative represented by Formula (2), $R^2$ is preferably a hydrogen atom, a hydroxy group (—OH), a methoxy group (—$OCH_3$), a fluorine atom (—F), or a methyl group (—$CH_3$).

<7> The method according to aspect <4>, wherein in the 4-aminobenzoic acid derivative represented by Formula (1) and the 3-hydroxy-4-aminobenzoic acid derivative represented by Formula (2), $R^1$ and $R^2$ are both hydrogen atoms.

<8> The method according to any of aspects <1> to <7>, wherein the contact between the 4-aminobenzoic acid and the microorganism is carried out by bringing a cell homogenate of the microorganism into contact with the 4-aminobenzoic acid at from 20° C. to 50° C., for from 5 minutes to 72 hours, preferably from 1 to 60 hours, and more preferably from 1 to 24 hours.

EXAMPLES

Hereinafter, the present invention will now be described in further detail based on examples but is not limited thereto.

Example 1: Production of Transformed Strain

PCR primers used in the Example are shown in Table 1.

TABLE 1

| Framer | Sequence (5'→3') | SEQ ID NO: |
|---|---|---|
| pET HFM122 F | GAAGGAGATATACATATGCGCACTCAGG TGGCTAT | 7 |
| pET HFM122 R | GTGGTGGTGGTGGTGTTATACGAGTGGC AGTCCTA | 8 |
| pET PHHYart_Pa F | GAAGGAGATATACATATGAAAACTCAGG TGGCTAT | 9 |
| pET PHHYart_Pa R | GTGGTGGTGGTGGTGTTACTCGATCTCC TCGTAAG | 10 |
| pET HFM689art F | GAAGGAGATATACATATGAAAACCCAGG TTGCCAT | 11 |
| pET HFM689art R | GTGGTGGTGGTGGTGTTAGACGGGCAGA CCGACGT | 12 |

TABLE 1-continued

| Framer | Sequence (5'→3') | SEQ ID NO: |
|---|---|---|
| pET21a vec R | ATGTATATCTCCTTCTTAAAGTTAAAC | 13 |
| pET21a vec F | CACCACCACCACCACCACTGAGATC | 14 |
| forCPCR pET21a F | CGAAATTAATACGACTCACTATAGGGGA ATTGTG | 15 |
| forCPCR pET21a R | CCAAGGGGTTATGCTAGTTATTGCTCAG | 16 |

<Production of Plasmid Vector>

Plasmids containing genes (SEQ ID Nos: 1, 3, and 5) encoding three 4-hydroxybenzoate hydroxylases (HFM122, HFM300, and HFM689) selected from among flavin monooxygenases were produced by artificial gene synthesis, and insert DNA fragments were synthesized by PCR using the plasmids as templates and using primers pET HFM122 F (SEQ ID NO: 7), pET HFM122 R (SEQ ID NO: 8), pET PHHYart_Pa F (SEQ ID NO: 9), pET PHHYart_Pa R (SEQ ID NO: 10), pET HFM689art F (SEQ ID NO: 11), and pET HFM689art R (SEQ ID NO: 12). Subsequently, a vector DNA fragment was amplified by PCR using plasmid pET21a as a template and primers pET21a vec R (SEQ ID NO: 13) and pET21a vec F (SEQ ID NO: 14). These fragments were respectively linked using In-Fusion HD Cloning Kit (Clontech) to construct plasmid vectors pET-HFM122, pET-HFM300, and pET-HFM689.

<Amplification of Plasmid Vector>

*Escherichia coli* DH5a strain (Nippon Gene Co., Ltd.) was transformed by a competent cell transformation method using the plasmid vectors pET-HFM122, pET-HFM300, and pET-HFM689 produced above. The resulting transformed cell solutions were applied to an LBamp agar culture medium (Facto Trypton: 1%, yeast extract: 0.5%, NaCl: 1%, ampicillin sodium: 50 μg/mL, agar: 1.5%) and were then left to stand at 37° C. overnight. The resulting colonies were subjected to PCR reaction using Sapphire Amp (Takara Bio Inc.) and primers forCPCR pET21a F (SEQ ID NO: 15) and forCPCR pET21a R (SEQ ID NO: 16), and a strain in which introduction of the target DNA fragment was observed was selected as a transformed strain. The transformed strain was inoculated in 1 mL of an LBamp liquid culture medium (Facto Trypton: 1%, yeast extract: 0.5%, NaCl: 1%, ampicillin sodium: 50 μg/mL) and was cultured at 37° C. overnight. Each plasmid vector was purified from this culture solution using High Pure Plasmid isolation Kit (Roche Life Science).

<Introduction of Plasmid Vector into Host Cell>

*Escherichia coli* BL21(DE3) strain (Nippon Gene Co., Ltd.) was transformed by a competent cell transformation method using the plasmid vectors pET-HFM122, pET-HFM300, and pET-HFM689 obtained above. The resulting transformed cell solutions were applied to an LBamp agar culture medium and were then left to stand at 37° C. overnight to obtain colonies as transformed strains (HFM122 strain, HFM300 strain, and HFM689 strain).

Example 2: Production of 3-Hydroxy-4-Aminobenzoic Acid Using Transformed Strain <Culture of Transformed Strain>

The HFM122 strain, HFM300 strain, and HFM689 strain obtained above were each inoculated in 1 mL of an LBamp liquid culture medium (Bacto Trypton: 1%, yeast extract: 0.5%, NaCl: 1%, ampicillin sodium: 50 μg/mL) and were cultured at 37° C. overnight. Each (100 μL) of the resulting culture solutions was inoculated in 10 mL of Overnight Express culture medium (Merck & Co., Ltd.) and was cultured at 37° C. for about 24 hours, and the cells were then collected by centrifugation.

<Preparation of Cell Homogenate>

The cells of the HFM122 strain, HFM300 strain, and HFM689 strain obtained above were suspended respectively in 1 mL of Bugbuster Protein Extraction Reagent (Merck & Co., Ltd.), the suspensions were shaken at 30° C. for 20 minutes, and insoluble matter was then removed by centrifugation to obtain cell homogenates.

Productivity of 3-hydroxy-4-aminobenzoic acid

To a 96-well assay plate (Iwaki Science Products Dept., AGC Techno Glass Co., Ltd.), each (80 μL) of cell homogenates of the HFM122 strain, HFM300 strain, and HFM689 strain obtained above was added and then 80 μL of a 100 mM phosphate buffer (pH 7.0), 20 μL of 100 mM NADPH, and 20 μL of 20 mM 4-aminobenzoic acid were added. After leaving to stand for 1 hour, the amount of 3-hydroxy-4-aminobenzoic acid was measured by the procedure described in Reference Example 1 described below.

The total protein amount in each cell homogenate was measured using Bio-Rad Protein Assay (Bio-Rad Laboratories, Inc.), and the productivity of 3-hydroxy-4-aminobenzoic acid and the improvement rate thereof in each of HFM122 strain and HFM689 strain were calculated by the following expressions.

3-Hydroxy-4-aminobenzoic acid productivity=(concentration of 3-hydroxy-4-aminobenzoic acid after reaction/total protein amount)

Productivity improvement rate (%)=(3-hydroxy-4-aminobenzoic acid productivity of *HFM*122 strain or *HFM*689 strain/3-hydroxy-4-aminobenzoic acid productivity of *HFM*300 strain)×100-100

The results are shown in Table 2. Improvements in the productivity by 46% and 114% were observed in HFM122 strain and HFM689 strain, respectively, compared to HFM300 strain suggested in Non Patent Literatures 3 and 4.

TABLE 2

| Strain name | Concentration of 3-hydroxy-4-aminobenzoic acid (g/L) | Productivity improvement rate (%) |
|---|---|---|
| HFM122 strain | 0.082 | 46 |
| HFM300 strain | 0.056 | — |
| HFM689 strain | 0.120 | 114 |

Reference Example 1: Quantitative Measurement of 3-hydroxy-4-aminobenzoic acid

The amount of 3-hydroxy-4-aminobenzoic acid after the reaction was measured by HPLC. The reaction solution to be subjected to HPLC analysis was appropriately diluted with 0.1% phosphoric acid, and insoluble matter was removed using AcroPrep 96 Filter Plate (0.2 μm GHP film, Nippon Pall Ltd.).

The HPLC apparatus used was LaChrom Elite (Hitachi High-Tech Corporation). Gradient elution was performed using L-column ODS (4.6 mm I.D.×50 cm, Chemical Evaluation and Research Institute, Japan) as the analysis column, phosphoric acid as eluent A, and 70% methanol as eluent B under conditions of a flow rate of 1.0 mL/min and a column temperature of 40° C. 3-Hydroxy-4-aminobenzoic acid was detected with a UV detector (detection wavelength: 280 nm). A concentration calibration curve was created using a standard sample [3-hydroxy-4-aminobenzoic acid (Distributor code: A1194, Tokyo Chemical Industry Co., Ltd.)], and 3-hydroxy-4-aminobenzoic acid was quantitatively measured based on the concentration calibration curve.

The invention claimed is:

1. A method for manufacturing a 3-hydroxy-4-aminobenzoic acid, comprising a step of bringing a 4-aminobenzoic acid into contact with a microorganism that produces polypeptide (A) or (B) shown below:

(A) a polypeptide consisting of the amino acid sequence of SEQ ID NO: 2 or a polypeptide consisting of an amino acid sequence that has at least 90% identity to the amino acid sequence of SEQ ID NO: 2 and has 4-hydroxybenzoate hydroxylase activity, or (B) a polypeptide consisting the an amino acid sequence of SEQ ID NO: 6 or a polypeptide consisting of an amino acid sequence that has at least 90% identity to the amino acid sequence of SEQ ID NO: 6 and has 4-hydroxybenzoate hydroxylase activity.

2. The method of claim 1, wherein the microorganism comprises the following polynucleotide (a) or (b) in an expressible state:

(a) a polynucleotide consisting of the nucleotide sequence of SEQ ID NO: 1 or a polynucleotide consisting of a nucleotide sequence that has at least 90% identity to the nucleotide sequence of SEQ ID NO: 1 and encodes a polypeptide having 4-hydroxybenzoate hydroxylase activity, or (b) a polynucleotide consisting of the nucleotide sequence of SEQ ID NO: 5 or a polynucleotide consisting of a nucleotide sequence that has at least 90% identity to the nucleotide sequence of SEQ ID NO: 5 and encodes a polypeptide having 4-hydroxybenzoate hydroxylase activity.

3. The method of claim 2, wherein the microorganism is *Escherichia coli* or *Corynebacterium*.

4. The method of claim 2, wherein the 4-aminobenzoic acid is a 4-aminobenzoic acid derivative having Formula (1) shown below:

(1)

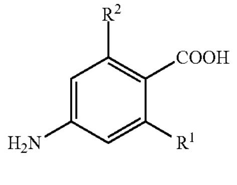

wherein $R^1$ is a hydrogen atom, a hydroxy group, a methoxy group, an amino group, a fluorine atom, a chlorine atom, a bromine atom, a iodine atom, a carboxy group, a methyl group, or an ethyl group; and $R^2$ is a hydrogen atom, a hydroxy group, a methoxy group, an amino group, a fluorine atom, a chlorine atom, a bromine atom, a iodine atom, a carboxy group, a methyl group, or an ethyl group, and the 3-hydroxy-4-aminobenzoic acid is a 3-hydroxy-4-aminobenzoic acid derivative having Formula (2) shown below:

(2)

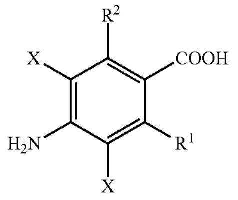

wherein $R^1$ and $R^2$ are the same as above; and one of the Xs is a hydrogen atom, and the other X is a hydroxy group.

5. The method of claim 2, wherein the contact between the 4-aminobenzoic acid and the microorganism is carried out by bringing a cell homogenate of the microorganism into contact with the 4-aminobenzoic acid at from 20° C. to 50° C., for from 5 minutes to 72 hours.

6. The method of claim 1, wherein the microorganism is *Escherichia coli* or *Corynebacterium*.

7. The method of claim 6, wherein the 4-aminobenzoic acid is a 4-aminobenzoic acid derivative having Formula (1) shown below:

(1)

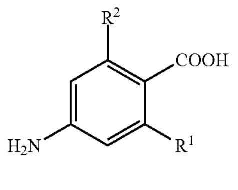

wherein $R^1$ is a hydrogen atom, a hydroxy group, a methoxy group, an amino group, a fluorine atom, a chlorine atom, a bromine atom, a iodine atom, a carboxy group, a methyl group, or an ethyl group; and $R^2$ is a hydrogen atom, a hydroxy group, a methoxy group, an amino group, a fluorine atom, a chlorine atom, a bromine atom, a iodine atom, a carboxy group, a methyl group, or an ethyl group, and the 3-hydroxy-4-aminobenzoic acid is a 3-hydroxy-4-aminobenzoic acid derivative having Formula (2) shown below:

(2)

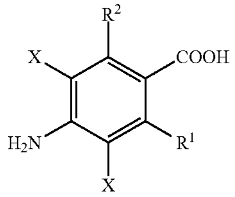

wherein $R^1$ and $R^2$ are the same as above; and one of Xs is a hydrogen atom, and the other a hydroxy group.

8. The method of claim 6, wherein the contact between the 4-aminobenzoic acid and the microorganism is carried out by bringing a cell homogenate of the microorganism into contact with the 4-aminobenzoic acid at from 20° C. to 50° C., for from 5 minutes to 72 hours.

9. The method of claim 1, wherein the 4-aminobenzoic acid is a 4-aminobenzoic acid derivative having Formula (1) shown below:

(1)

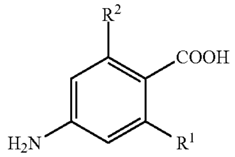

wherein $R^1$ is a hydrogen atom, a hydroxy group, a methoxy group, an amino group, a fluorine atom, a chlorine atom, a bromine atom, a iodine atom, a carboxy group, a methyl group, or an ethyl group; and $R^2$ is a hydrogen atom, a hydroxy group, a methoxy group, an amino group, a fluorine atom, a chlorine atom, a bromine atom, a iodine atom, a carboxy group, a methyl group, or an ethyl group, and the 3-hydroxy-4-aminobenzoic acid is a 3-hydroxy-4-aminobenzoic acid derivative having Formula (2) shown below:

(2)

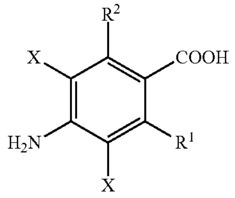

wherein $R^1$ and $R^2$ are the same as above; and one of the Xs is a hydrogen atom, and the other X is a hydroxy group.

10. The method of claim 9, wherein in the 4-aminobenzoic acid derivative having Formula (1) and the 3-hydroxy-4-aminobenzoic acid derivative having Formula (2), le is a hydrogen atom, a hydroxy group, a methoxy group, a fluorine atom, or a methyl group.

11. The method of claim 9, wherein in the 4-aminobenzoic acid derivative having Formula (1) and the 3-hydroxy-4-aminobenzoic acid derivative having Formula (2), $R^2$ is a hydrogen atom, a hydroxy group, a methoxy group, a fluorine atom, or a methyl group.

12. The method of claim 9, wherein in the 4-aminobenzoic acid derivative having Formula (1) and the 3-hydroxy-4-aminobenzoic acid derivative having Formula (2), $R^1$ and $R^2$ are both hydrogen atoms.

13. The method of claim 1, wherein the contact between the 4-aminobenzoic acid and the microorganism is carried out by bringing a cell homogenate of the microorganism into contact with the 4-aminobenzoic acid at from 20° C. to 50° C., for from 5 minutes to 72 hours.

* * * * *

UNITED STATES PATENT AND TRADEMARK OFFICE

CERTIFICATE OF CORRECTION

PATENT NO. : 11,312,980 B2
APPLICATION NO. : 17/269689
DATED : April 26, 2022
INVENTOR(S) : Nonaka et al.

It is certified that error appears in the above-identified patent and that said Letters Patent is hereby corrected as shown below:

In the Claims

Column 25 Line 30 Claim 1, replace "consisting the an" with --consisting of the--.

Column 26 Line 66 Claim 7, replace "and the other a hydrogen group" with --and the other is a hydrogen group--.

Column 28 Line 23 Claim 10, replace "le is a hydrogen atom" with --$R^1$ is a hydrogen atom--.

Signed and Sealed this
Twenty-first Day of June, 2022

Katherine Kelly Vidal

Katherine Kelly Vidal
*Director of the United States Patent and Trademark Office*